US008556422B2

(12) United States Patent
Kishimoto et al.

(10) Patent No.: US 8,556,422 B2
(45) Date of Patent: Oct. 15, 2013

(54) FLUORESCENCE IMAGE ACQUISITION METHOD, FLUORESCENCE IMAGE ACQUISITION PROGRAM, AND FLUORESCENCE IMAGE ACQUISITION APPARATUS

(75) Inventors: Takuya Kishimoto, Tokyo (JP); Sakuya Tamada, Tokyo (JP); Akio Yasuda, Tokyo (JP); Kyoko Ohno, Tokyo (JP); Ikuo Morita, Tokyo (JP)

(73) Assignees: Sony Coporation, Tokyo (JP); National University Corporation Tokyo Medical and Dental University, Tokyo (JP)

( * ) Notice: Subject to any disclaimer, the term of this patent is extended or adjusted under 35 U.S.C. 154(b) by 148 days.

(21) Appl. No.: 13/071,136

(22) Filed: Mar. 24, 2011

(65) Prior Publication Data

US 2011/0242485 A1    Oct. 6, 2011

(30) Foreign Application Priority Data

Mar. 31, 2010    (JP) ................................ P2010-081400

(51) Int. Cl.
*A61B 3/14*    (2006.01)
*A61B 3/00*    (2006.01)

(52) U.S. Cl.
USPC .......................................... 351/206; 351/221

(58) Field of Classification Search
USPC ................................................ 351/206–208
See application file for complete search history.

(56) References Cited

U.S. PATENT DOCUMENTS 5,279,298 A * 1/1994 Flower .......................... 600/321
2011/0116041 A1* 5/2011 Hartung et al. ............... 351/206
2012/0155735 A1* 6/2012 Friedman et al. ............. 382/131

FOREIGN PATENT DOCUMENTS

JP    2008-295804    12/2008

OTHER PUBLICATIONS

"The potential role of amyloid b in the pathogenesis of age-related macular degeneration", The Journal of Clinical Investigation, Oct. 2005, vol. 115, No. 10, pp. 2793-2800.
"Amyloid-b is found in drusen from some age-related macular degeneration retinas, but not in drusen from normal retinas", Molecular Visioin 2003, vol. 9, pp. 184-190.

* cited by examiner

*Primary Examiner* — Jordan Schwartz
(74) *Attorney, Agent, or Firm* — K&L Gates LLP

(57) ABSTRACT

A fluorescence image acquisition method including: irradiating an eyeground with a short-pulse beam of light for exciting a fluorescent dye; setting the time point of emission of the light as a reference, measuring the intensities of luminescence of the fluorescent dye at two different times which are predetermined periods of time after the reference, determining the ratio between the intensities of luminescence at the two different times, and detecting the intensity of luminescence of the fluorescent dye having marked a target by using the ratio; and generating a fluorescence image of the fluorescent dye having marked the target, based on the results of detection by the detecting step.

5 Claims, 4 Drawing Sheets

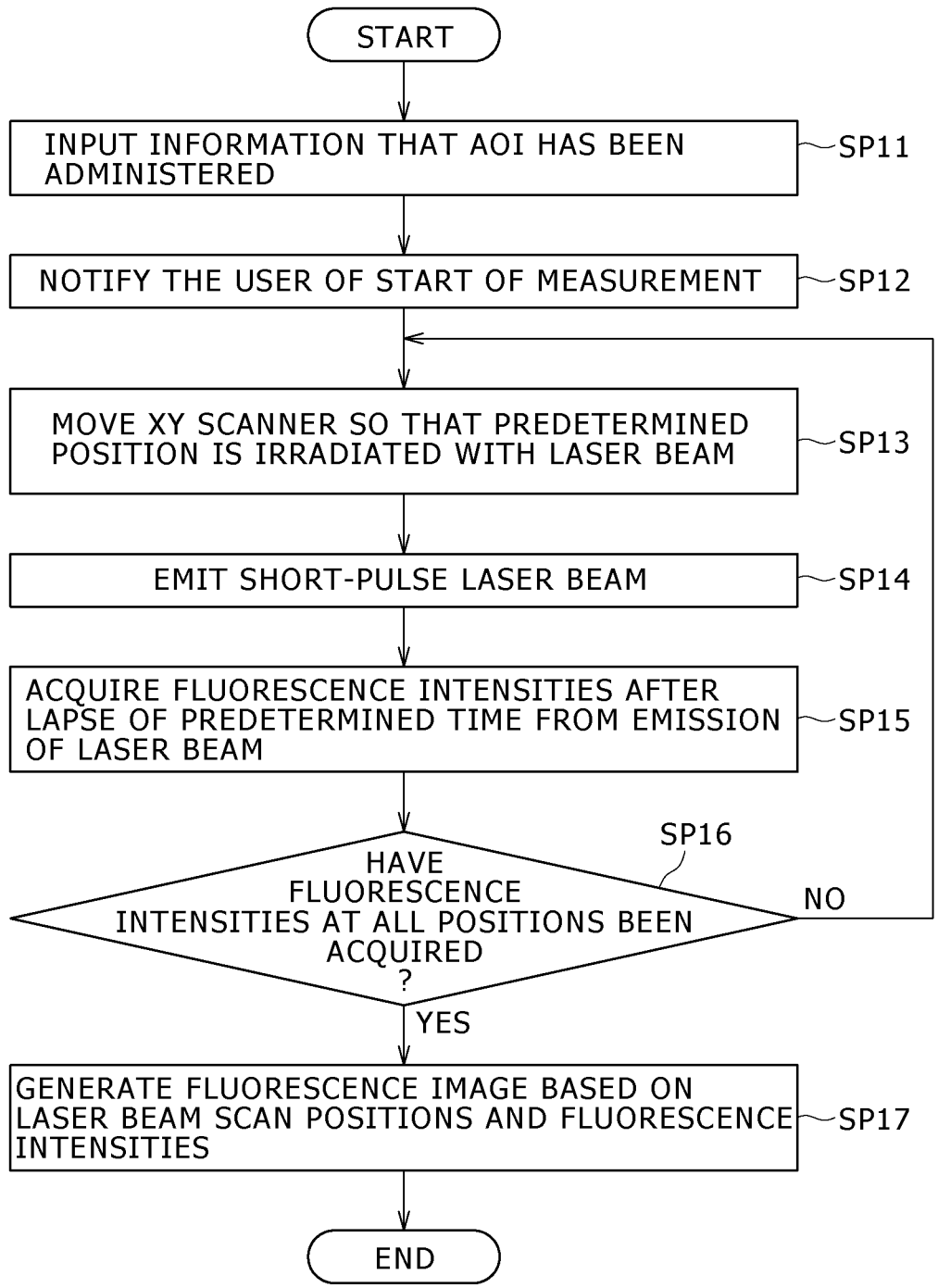

FLUORESCENCE IMAGE ACQUISITION METHOD, FLUORESCENCE IMAGE ACQUISITION PROGRAM, AND FLUORESCENCE IMAGE ACQUISITION APPARATUS

CROSS REFERENCES TO RELATED APPLICATIONS

The present application claims priority to Japanese Patent Application JP 2010-081400 filed on Mar. 31, 2010, the entire contents of which is hereby incorporated by reference.

BACKGROUND

The present disclosure relates to a fluorescence image acquisition method, a fluorescence image acquisition program, and a fluorescence image acquisition apparatus, and is preferable for application to, for example, examination of age-related macular degeneration.

Age-related macular degeneration (AMD) is one of diseases constituting major causes of visual impairment and loss of eyesight, and is classified generally into the exudative type and the atrophic type. The atrophic AMD is a disease in which the yellow spot tissues are gradually atrophied with aging, to cause a lowering in eyesight or the like on a long-term basis. On the other hand, the exudative AMD is a disease in which neovascularization from the choroids occurs at the yellow spot, and, since the newly formed blood vessels are brittle, bleeding occurs under the pigmented layer of retina or under the retina, to cause functional disorders at the yellow spot part.

Normally, the waste products formed by metabolism are digested in the pigmented layer of retina located between the retina and the choroids. However, when the functions of the pigmented layer of retina are lowered with aging, the waste products would not be digested but be accumulated (as drusen) on the Bruch's membrane, resulting in chronic inflammation. In this case, at the inflammation part, an agent capable of promoting neovascularization is released in order to suppress the inflammation. Attendant on this, new blood vessels are generated from the choroids. In this manner, the exudative AMD is brought about.

In view of this, there has been proposed an apparatus for picking up an image of a subject's eyeground and detecting a lesion part, such as waste product, from the eyeground image (see, for example, Japanese Patent Laid-open No. 2008-295804 hereinafter referred to as Patent Document 1).

SUMMARY

Meanwhile, Patent Document 1 discloses that not only a fundus camera but also a scanning type laser ophthalmoscope and the like can be applied as a device for acquiring an eyeground image. In the scanning type laser ophthalmoscope, the eyeground is irradiated with a beam of light in a scanning manner, and the reflected light or fluorescent light from a predetermined part is received by an imaging device, thereby obtaining the eyeground image.

The eyeground image acquired by the scanning type laser ophthalmoscope can be a fluorescent image which is higher in definition than the images obtained by the fundus camera. In this case, however, the lesion part is detected based on morphological findings, like in the case of the fundus camera.

Thus, in the cases of the devices according to the related art, the detection of a lesion part from the eyeground image acquired is based on the morphological findings. Therefore, it has been impossible to find the lesion part early and accurately before neovascularization is observed.

Thus, there is a need for a fluorescence image acquisition method, a fluorescence image acquisition program and a fluorescence image acquisition apparatus by which a lesion part at the eyeground can be found at an early stage and accurately.

According to one embodiment, there is provided a fluorescence image acquisition method including the steps of: irradiating an eyeground with a short-pulse beam of light for exciting a fluorescent dye which is linked specifically to a target; setting the time point of emission of the light as a reference, measuring the intensities of luminescence of the fluorescent dye at two different times which are predetermined periods of time after the reference, determining the ratio between the intensities of luminescence at the two different times, and detecting the intensity of luminescence of the fluorescent dye having marked the target by using the ratio; and generating a fluorescence image of the fluorescent dye having marked the target, based on the results of detection by the detecting step.

In addition, according to another embodiment, there is provided a fluorescence image acquisition program wherein a computer is made to execute the steps of: irradiating an eyeground with a short-pulse beam of light for exciting a fluorescent dye; setting the time point of emission of the light as a reference, measuring the intensities of luminescence of the fluorescent dye at two different times which are predetermined periods of time after the reference, and detecting the intensity of luminescence of the fluorescent dye having marked a target by using the ratio between the intensities of luminescence at the two different times; and generating a fluorescence image of the fluorescent dye having marked the target, based on the results of detection by the detecting step.

Further, according to a further embodiment, there is provided a fluorescence image acquisition apparatus including: a light source operable to emit a short-pulse beam of light for exciting a fluorescent dye; a light source control section operable to irradiate an eyeground with the light from the light source; a detection section operable to set the time point of emission of the light as a reference, measure the intensities of luminescence of the fluorescent dye at two different times which are predetermined periods of time after the reference, and detect the intensity of luminescence of the fluorescent dye having marked a target by using the ratio between the intensities of luminescence at the two different times; and a generation section operable to generate a fluorescence image of the fluorescent dye having marked the target, based on the results of detection by the detection section.

According to these embodiments, it is possible to acquire a fluorescence image reflecting only the fluorescent dye with which the target has been marked, based on the intensities of luminescence at the two times. Therefore, the fluorescence image of the fluorescent dye which has marked the target can be obtained accurately, without reflecting on the image the fluorescent dye which has not marked the target. Besides, in the case where a protein appearing at a lesion part of the eyeground at an early stage is adopted as the target which is marked with the fluorescent dye, it is possible to visualize the protein through acquisition of the fluorescence image, offering a material ground for examination of the eyeground. With the material ground provided in addition to morphological findings, a lesion part of the eyeground can be found at an early stage.

According to yet another embodiment, there is provided a fluorescence image acquisition method including the steps of: inputting information that a fluorescent dye has been administered into a subject; starting measurement after a predetermined lapse of time from the inputting by the inputting step; irradiating the subject's eyeground with light for exciting the fluorescent dye; measuring the intensity of luminescence of the fluorescent dye which fluoresces when exited by the light; and generating a fluorescence image based on the intensity of luminescence.

In addition, according to a further embodiment, there is provided a fluorescence image acquisition program wherein a computer is made to execute the steps of: inputting information that a fluorescent dye has been administered into a subject; starting measurement after a predetermined lapse of time from the inputting by the inputting step; irradiating the subject's eyeground with light for exciting the fluorescent dye; measuring the intensity of luminescence of the fluorescent dye which fluoresces when exited by the light; and generating a fluorescence image based on the intensity of luminescence.

According to another embodiment, there is provided a fluorescence image acquisition apparatus including: a light source operable to emit a short-pulse beam of light for exciting a fluorescent dye; a console unit operable to input information that the fluorescent dye has been administered into a subject; a measurement start control section operable to start measurement after a predetermined lapse of time from the inputting by the console unit; a light source control section operable to irradiate the subject's eyeground with the light for exciting the fluorescent dye; a measurement section operable to measure the intensity of fluorescence of the fluorescent dye which fluoresces when excited by the light; and a generation section operable to generate a fluorescence image based on the intensity of fluorescence.

According to these embodiments, the fluorescent dye which has not marked the target is discharged, and an image of only the fluorescent dye which has marked the target can be acquired. Therefore, the fluorescence image of the fluorescent dye with which the target has been marked can be acquired with high accuracy. In addition, in the case where a protein appearing in a lesion part of the eyeground at an early stage is adopted as the target and is marked with the fluorescent dye, the protein can be visualized by obtaining the fluorescence image, offering a material ground for examination of the eyeground. With the material ground thus provided in addition to morphological findings, a lesion part of the eyeground can be found at an early stage.

According to some of the above-mentioned embodiments, it is possible to acquire a fluorescence image of only the fluorescent dye with which the target has been marked, based on the intensities of luminescence at two times. Therefore, the fluorescence image of the fluorescent dye which has marked the target can be accurately obtained, without reflecting the fluorescent dye which has not marked the target. Besides, in the case where a protein appearing in a lesion part of the eyeground at an early stage is adopted as the target and is marked with the fluorescent dye, the protein can be visualized by obtaining the fluorescence image of the fluorescent dye, offering a material ground for examination of the eyeground. With the material ground thus provided in addition to morphological findings, the lesion part of the eyeground can be found at an early stage. Consequently, it is possible to realize a fluorescence image acquisition method, a fluorescence image acquisition program and a fluorescence image acquisition apparatus by which a lesion part of an eyeground can be found at an early stage and accurately.

In addition, the fluorescent dye which has not marked the target is discharged, and an image of only the fluorescent dye which has marked the target can be obtained. Therefore, the fluorescence image of the fluorescent dye with which the target has been marked can be acquired with high accuracy.

Besides, where a protein appearing at a lesion part of the eyeground at an early stage is adopted as the target to be marked with the fluorescent dye, the protein can be visualized by obtaining the fluorescence image of the fluorescent dye, offering a material ground for examination of the eyeground. With the material ground thus provided in addition to morphological findings, a lesion part of the eyeground can be found early. Thus, it is possible to realize a fluorescence image acquisition method, a fluorescence image acquisition program and a fluorescence image acquisition apparatus by which a lesion part of an eyeground can be found at an early stage and accurately.

Additional features and advantages are described herein, and will be apparent from the following Detailed Description and the figures.

BRIEF DESCRIPTION OF THE FIGURES

FIG. 6 is a flow chart for illustrating the procedure of a fluorescence image acquisition process according to another embodiment.

DETAILED DESCRIPTION

Embodiments will be described below. Incidentally, the description will be made in the following order.

1. First Embodiment
2. Another Embodiment

1. First Embodiment

[1-1. Configuration of Fluorescence Image Acquisition Apparatus]

Figure 1:
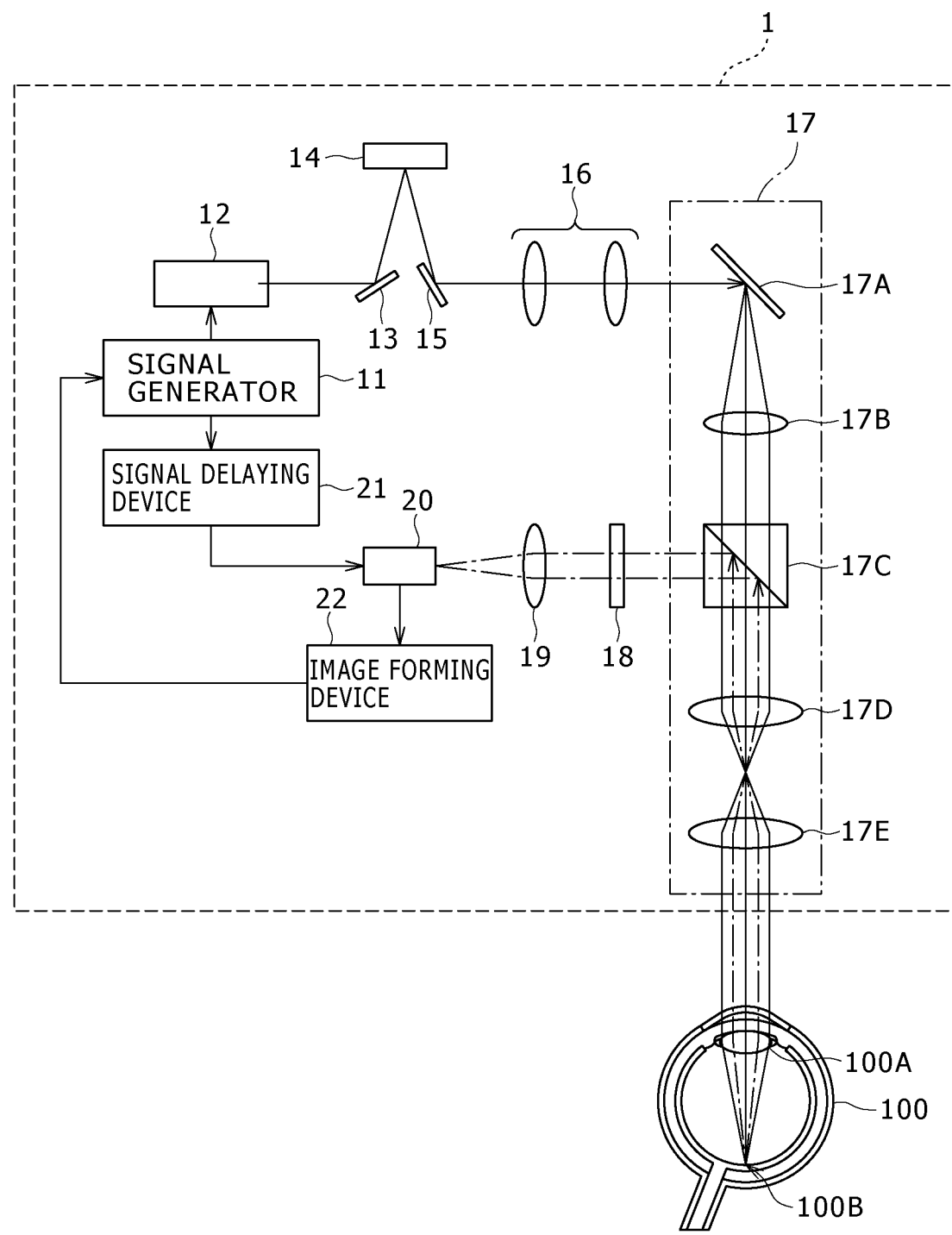
FIG. 1 is a block diagram showing a fluorescence image acquisition apparatus according to an embodiment.

FIG. 1 shows a fluorescence image acquisition apparatus 1 according to this first embodiment. The fluorescence image acquisition apparatus 1 is used in examining the presence or absence of drusen accumulated at a yellow spot of an eyeground.

Specifically, it is known that amyloid β protein is accumulated at the yellow spot of the eyeground at the stage where drusen is formed. In the amyloid β protein, β sheet structures are stacked in layers to form an aggregate (see Yoshida T. et al, "The potential role of amyloid b in the pathogenesis of age-related macular degeneration", The Journal of Clinical Investigation, Vol. 115, 2005, pp. 2793-2800 and Dentchev T. et al, "Amyloid b is found in drusen from some age-related macular degeneration retinas, but not in drusen from normal retinas.", Molecular Vision, Vol. 9, 2003, pp. 184-190).

On the other hand, in detection of the presence or absence of amyloid β protein, which is said to be a cause of Alzheimer's disease, by a PET (positron emission tomography) or the like, AOI (4,8-dimethyl-2,3,8,9,10-pentahydro-1,6,11-trioxa-4-azonia-8,13-diazapentacene tetrafluoroborate) is used as a marker compound. The AOI is a fluorescent dye, and is specifically linked only to amyloid β protein. Other substances than AOI which are also applicable as a marker compound capable of fluorescence through specific linkage to amyloid β protein include BF227 (2-[2-(2-dimethylaminothiazol-5-yl)ethenyl]-6[2-(fluoro)ethoxy]benzoxazole), FSB ((trans,trans)-1-fluoro-2,5-bis(3-hydroxycarbonyl-4-hydroxy)styrylbenzene), and PIB (2-[4'-(Methylamino)phenyl]-6-hydroxybenzothiazole).

Therefore, in the case where drusen is formed at a subject's yellow spot, administration of AOI into the subject results in that the AOI is linked to amyloid β protein contained in the drusen.

In view of this, the fluorescence image acquisition apparatus 1 is so designed that the eyeground of the subject preliminarily dosed with AOI is irradiated with light for exciting the AOI, and the fluorescence image of the eyeground in this instance is acquired, whereby the drusen accumulation as a beginning-stage symptom of age-related macular degeneration can be found earlier than in the related art.

The fluorescence image acquisition apparatus 1 includes a signal generator 11, a short-pulse laser 12, a reflecting mirror 13, a wavefront compensating optic element 14, a reflecting mirror 15, a beam diameter regulator 16, a laser scanning ophthalmoscope 17, a bandpass filter 18, a condenser lens 19, a photodetector 20, a signal delaying device 21 and an image forming device 22.

The image forming device 22 controls the signal generator 11, the wavefront compensating optic element 14, the beam diameter regulator 16, the laser scanning ophthalmoscope 17 and the signal delaying device 21, as required. This will be detailed later.

The signal generator 11, upon receiving a laser beam output command from the image forming device 22, sends an emission signal for outputting a laser beam with a short pulse of, for example, 10 [ps] to the short-pulse laser 12, and also to the signal delaying device 21.

The short-pulse laser 12 is designed to be able to emit a pulsed laser beam based on the emission signal supplied from the signal generator 11, with a wavelength in the range of 620 to 1000 [nm]. The pulse width is arbitrary set within the range of 10 [f sec] to 100 [p sec].

Specifically, where the laser beam emitted from the short-pulse laser 12 has a wavelength of 633 [nm] and a pulse width of about 10 [ps], then the output stability is about ±5[%], the repetition frequency is 80 [MHz], and the average beam output is about 200 [mW]. The output is controlled to such an energy as not to damage the eyeground.

The laser beam emitted from the short-pulse laser 12 is reflected by the reflecting mirror 13, before being incident on the wavefront compensating optic element 14. The wavefront compensating optic element 14 corrects the wavefront aberration of the incident laser beam, and reflects the thus corrected laser beam to guide it to the reflecting mirror 15. In this manner, the wavefront compensating optic element 14 is able to correct the wavefront aberration arising from an individual difference in a crystalline lens 100A.

The laser beam reflected by the reflecting mirror 15 is transmitted through the beam diameter regulator 16 for controlling the beam diameter, to be incident on the laser scanning ophthalmoscope 17. The beam diameter regulator 16 is composed, for example, of two lenses so that the beam diameter of the laser beam can be controlled by moving one of the lenses in the optical axis direction.

The laser scanning ophthalmoscope 17 includes an XY scanner 17A including, for example, a galvano-mirror for scanning the laser beam on an XY plane (a plane orthogonal to the optical axis, at the eyeground 100B), an Fθ lens 17B, a dichroic mirror 17C, and aberration correcting convex lenses 17D, 17E.

The laser beam controlled in beam diameter by the beam diameter regulator 16 is reflected by the XY scanner 17A, is transmitted through the Fθ lens 17B and the dichroic mirror 17C, and then through the aberration correcting convex lenses 17D and 17E, to be incident on the eye 100.

The laser beam entering the eye 100 is condensed by the crystalline lens 100A of the eye 100, to be radiated onto the eyeground 100B inclusive of the yellow spot. Incidentally, the energy of the laser beam entering the eye 100 is desirably not more than 1 [mW].

In the case where the AOI as the fluorescent dye to be excited by the laser beam of a wavelength of 633 [nm] is present at the eyeground 100B, the AOI is excited by the laser beam emitted from the fluorescence image acquisition apparatus 1.

The AOI excited by the laser beam fluoresces at a wavelength of about 670 [nm]. The light obtained by this fluorescence (the light will hereafter be referred to also as fluorescent light) is transmitted through the crystalline lens 100A and the aberration correcting convex lenses 17D, 17E, to be reflected by the dichroic mirror 17C.

The dichroic mirror 17C is so designed as, for example, to reflect light having a wavelength of not less than 650 [nm] and to transmit light having a wavelength of less than 650 [nm]. Therefore, the dichroic mirror 17C transmits the laser beam emitted from the short-pulse laser 12, but reflects the fluorescent light.

The fluorescent light reflected by the dichroic mirror 17C is transmitted through the bandpass filter 18, and is condensed by the condenser lens 19, before reaching the photodetector 20. The bandpass filter 18 is so designed as, for example, to transmit light in a wavelength region having a center wavelength of 670 [nm] and a wavelength band of 50 [nm].

The photodetector 20 has, for example, an MCP (Multi Channel Plat), by which the fluorescent light condensed by the condenser lens 19 is received according to the timing of a delay signal supplied from the signal delaying device 21, and the intensity of the fluorescent light thus obtained (the intensity will hereafter referred to also as fluorescence intensity) is outputted to the image forming device 22. Incidentally, the photodetector 20 measures the fluorescence intensity, for example, according to the number of single photons at the measurement timing for a predetermined number of measurements by a TCSPC (time-correlated single-photon counting) method.

The signal delaying device 21 sends to the photodetector 20 a delay signal for ensuring that, while the time point of supply of the emission signal from the signal generator 11 is taken as a reference, the fluorescence intensity of the luminescent light impinging on the photodetector 20 is measured after a predetermined lapse of time from the reference.

The image forming device 22 forms a fluorescence image based on the relationship between the position of scan of the laser beam by the XY scanner 17A and the fluorescence intensity measured by the photodetector 20, and stores the data on the fluorescence image in a storage unit.

[1-2. Configuration of Image Forming Device]

Figure 2:
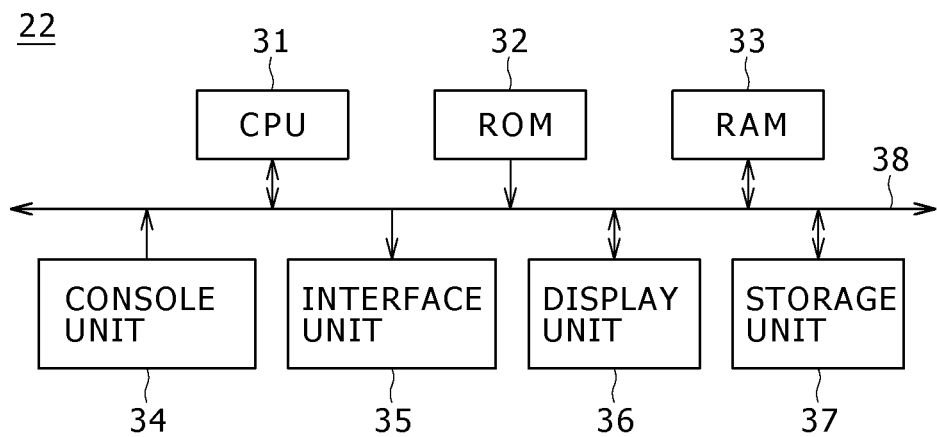
FIG. 2 is a block diagram showing the configuration of an image forming device in an embodiment.

Now, the configuration of the image forming device 22 will be described below. As shown in FIG. 2, the image forming device 22 is configured by connecting various kinds of hardware to a CPU (central processing unit) 31 in charge of control.

Specifically, a ROM (read only memory) 32, a RAM (random access memory) 33 serving as a working memory for the CPU 31, a console unit 34 for inputting commands according to the user's operation, an interface unit 35, a display unit 36 and a storage unit 37 are connected to the CPU 31 through a bus 38.

Programs for executing a variety of processes are stored in the ROM 32. To the interface unit 35 are connected the signal generator 11, the wavefront compensating optic element 14, the beam diameter regulator 16, the XY scanner 17A, the signal delaying device 21 and the like.

A liquid crystal display, an EL (electroluminescence) display, a plasma display or the like is applied as the display unit 36. A magnetic disk, represented by a HD (hard disk), or a semiconductor memory, an optical disk or the like is applied as the storage unit 37.

The CPU 31 deploys a program corresponding to the commands given from the console unit 34, which program is selected from among the plurality of programs stored in the ROM 32, into the RAM 33 and controls the display unit 36 and the storage unit 37, as required, according to the program thus deployed.

In addition, the CPU 31 controls the signal generator 11, the wavefront compensating optic element 14, the beam diameter regulator 16, the XY scanner 17A, the signal delaying device 21 and the like, as required, according to the deployed program.

[1-3. Fluorescence Image Acquisition Process]

Now, a fluorescence image acquisition process for acquiring a fluorescence image of the eyeground 100B of the subject dosed with AOI will be described below.

Incidentally, before carrying out the fluorescence image acquisition process, the AOI as the fluorescent marker compound is dissolved in physiological saline in a concentration of, for example, 2 [mg/kg], and the solution is administered into the subject by intravenous injection, for example.

Then, it is confirmed that the AOI has reached the eyeground 100B of the subject dosed with the AOI, and, after a predetermined lapse of time, the fluorescence image acquisition process is carried out, to obtain fluorescence images of the eyeground as a whole and a yellow spot part.

Here, the AOI administered into the subject, upon reaching the eyeground 100B, is bonded to amyloid β protein in the case where amyloid β protein has been accumulated at the yellow spot of the eyeground 100B. The AOI thus linked to the amyloid β protein is limited in motion, whereby the life of fluorescence thereof is prolonged.

On the other hand, the AOI which has not been bonded to the amyloid β protein is metabolized by the kidney and the liver, to be mostly excreted in about 120 minutes from the administration.

However, it cannot be said that, even after about 120 minutes from the administration, the AOI not bonded to the amyloid β protein has been completely removed from the yellow spot. Besides, the intensity of the laser beam should be lowered for the purpose of alleviating the burden on the subject.

In the methods according to the related art, therefore, the AOI not having bonded to the amyloid β protein may be reflected on the fluorescence image obtained. In addition, since the intensity of the laser beam used is low, the S/N (signal-to-noise) ratio is poor due to the influence of noise or the like. In the related-art methods, accordingly, it may become impossible to distinguish the AOI having bonded to the amyloid β protein from the fluorescence image obtained.

In view of this, the fluorescence image acquisition apparatus 1 acquires a fluorescence image, based on the difference in life of fluorescence between the AOI bonded to the amyloid β protein and the AOI not bonded to the amyloid β protein.

Specifically, in the fluorescence image acquisition apparatus 1, the fluorescence image acquisition process is executed after a predetermined lapse of time (120 minutes) from the time when it is confirmed that the AOI has reached the eyeground 100B of the subject dosed with the AOI.

Figure 3:
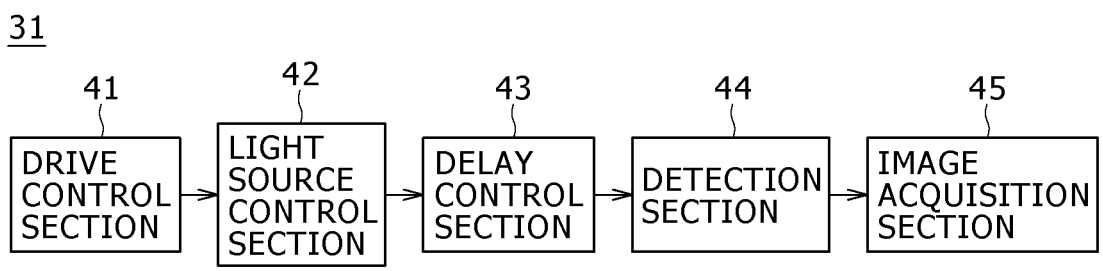
FIG. 3 is a block diagram showing the functional configuration of a CPU for executing a fluorescence image acquisition process.

When supplied with run commands for the fluorescence image acquisition process from the console unit 34, the CPU 31 functions as a drive control section 41, a light source control section 42, a delay control section 43, a detection section 44 and an image acquisition section 45 as shown in FIG. 3, according to the program corresponding to the run commands.

The drive control section 41 drives the XY scanner 17A, and moves the XY scanner 17A so that a predetermined position is irradiated with the laser beam.

The light source control section 42 sends to the signal generator 11 an output signal for causing the short-pulse laser 12 to emit a laser beam. Upon being supplied with the output signal from the light source control section 42, the signal generator 11 sends an emission signal to the short-pulse laser 12 to make the short-pulse laser 12 emit a short-pulse laser beam, and sends the emission signal to the signal delaying device 21.

The delay control section 43 determines a timing for measurement of the fluorescence intensity by the photodetector 20, according to an input from the console unit 34, for example, and sends a signal indicative of the timing to the signal delaying device 21.

Based on the signal supplied from the delay control section 43, the signal delaying device 21, taking as a reference the time point of being supplied with the emission signal from the signal generator 11, sends a delay signal to the photodetector 20 at times t1 and t2 which are predetermined periods of time after the reference. The photodetector 20 measures the fluorescence intensity at the timings of being supplied with the delay signal, that is, at times t1 and t2.

Incidentally, times t1 and t2 are set to be shorter than the life of fluorescence of AOI. Besides, while time t1 is set at the time when the fluorescence intensity has a peak value in this embodiment, it may be set otherwise.

Subsequently, the CPU 31 actuates the drive control section 41 to move the XY scanner 17A so that the position of irradiation with the laser beam is changed, and causes the measurement of the fluorescence intensity in the position to be carried out at times t1 and t2 under the control of the light source control section 42 and the delay control section 43.

In this manner, the CPU 31 causes the XY scanner 17A to scan the laser beam within a predetermined imaging range, and causes the photodetector 20 to measure the fluorescence intensities in individual positions at times t1 and t2 with reference to the time point of emission of the laser beam.

Meanwhile, as above-mentioned, there is a difference in life of fluorescence between the AOI which has been bonded to the amyloid β protein and the AOI which has not been bonded to the amyloid β protein. The relationship between the life of fluorescence of the AOI bonded to the amyloid β protein and that of the AOI not bonded to amyloid β protein is shown in FIG. 4.

Figure 4:
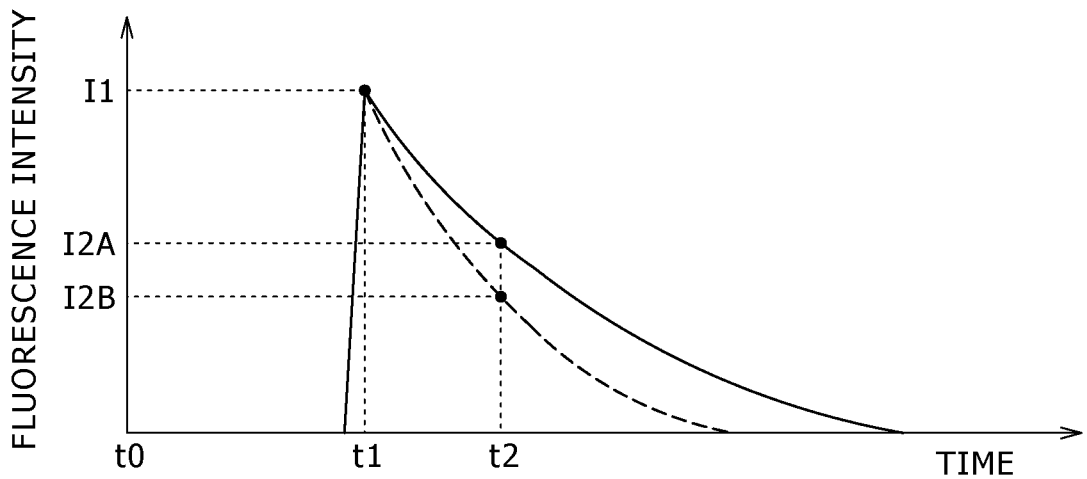
FIG. 4 is a graph showing variations in life of fluorescence.

In FIG. 4, time t0 indicates the time when the laser beam is emitted; the solid line indicates the fluorescence intensity of the AOI bonded to the amyloid β protein; and broken line indicates the fluorescence intensity of the AOI not bonded to the amyloid β protein.

The fluorescence intensity I1 measured at time t1 by the photodetector 20 is the peak value of the fluorescence intensity of the excited AOI, the value being common for both the AOI bonded to amyloid β protein and the AOI not bonded to amyloid β protein.

However, since the difference in life of fluorescence, the fluorescence intensity I2A of the AOI bonded to amyloid β protein at time t2 is higher than the fluorescence intensity I2B of the AOI not bonded to amyloid β protein at time t2. Incidentally, where the fluorescence intensities I2A and I2B are not to be distinguished from each other, the fluorescence intensity will be referred to also as fluorescence intensity I2.

The detection section 44 calculates the ratio (I2/I1) between the fluorescence intensity I1 at time t1 and the fluorescence intensity I2 at time t2, for all the positions of scan by the XY scanner 17A, and compares the ratios with a threshold.

The threshold is set at a value which is smaller than the ratio (I2A/I1) between the fluorescence intensity I1 and the fluorescence intensity I2A and is not less than the ratio (I2B/I1) between the fluorescence intensity I1 and the fluorescence intensity I2B.

In the case where the ratio between the fluorescence intensity I1 at time t1 and the fluorescence intensity I2 at time t2 is not less than the threshold, the photodetector 44 determines that the fluorescence intensity is that of the AOI bonded to amyloid β protein, and detects the relevant position as a position where the AOI bonded to amyloid β protein is present.

The image acquisition section 45 forms a fluorescence image in which the luminance values at the positions where the AOI bonded to amyloid β protein is present are luminance values according to the fluorescence intensities I1 at the positions, whereas the luminance values at other positions are 0 (black).

The image acquisition section 45 acquires the data on the fluorescence image thus formed, and stores the data into the storage unit 37. In addition, the image acquisition section 45 displays the fluorescence image on the display unit 36, according to an operation on the console unit 34.

[1-4. Procedure of Fluorescence Image Acquisition Process]

Figure 5:
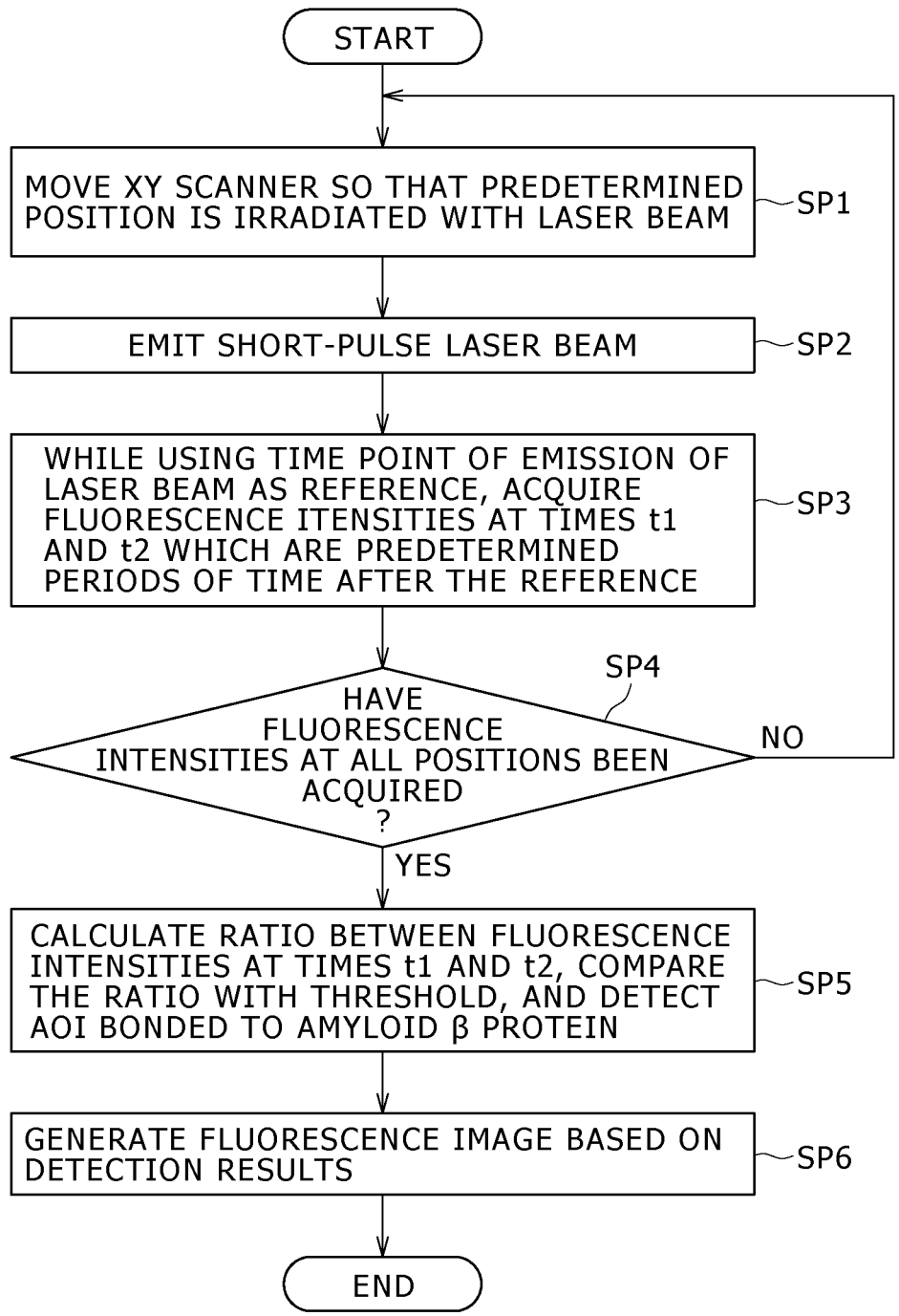
FIG. 5 is a flow chart for illustrating the procedure of the fluorescence image acquisition process.

Now, the procedure of the fluorescence image acquisition process as above will be described using a flow chart shown in FIG. 5.

In practice, the CPU 31 starts control from the START step of routine RT1, and goes to the next step SP1. In step SP1, the CPU 31 drives the XY scanner 17A to move so that a predetermined position is irradiated with the laser beam, and then goes to the subsequent step SP2.

In step SP2, the CPU 31 sends an output signal to the signal generator 11. The short-pulse laser 12 is actuated through the signal generator 11 to emit a short-pulse laser beam, and the CPU 31 goes to the next step SP3.

In step SP3, the CPU 31 acquires the fluorescence intensities I1 and I2 measured by the photodetector 20 at times t1 and t2 which are predetermined periods of time after the time point when the emission signal is supplied from the signal generator 11. Then, the CPU 31 goes to the subsequent step SP4.

In SP4, the CPU 31 determines whether or not the fluorescence intensities at all positions in the imaging range have been acquired. If the determination result is negative (NO), the control returns to step SP1, and steps SP1 to SP4 are repeated until the fluorescence intensities at all positions are acquired.

On the other hand, if the result of determination in step SP4 is affirmative (YES), it means that the fluorescence intensities at all positions in the imaging range have been acquired, and the CPU 31 goes to the next step SP5.

In step SP5, the CPU 31 compares the ratio between the fluorescence intensities I1 and I2 at times t1 and t2 with the threshold, thereby detecting the fluorescence intensities of the AOI bonded to amyloid β protein, and then goes to the subsequent step SP6.

In step SP6, the CPU 31 forms a fluorescence image of the AOI bonded to amyloid β protein, based on the results of detection in step SP5. Then, the CPU 31 goes to the next step, finishing the process.

[1-5. Operation and Effect]

In the fluorescence image acquisition apparatus 1 configured as above, the short-pulse laser 12 is actuated through the signal generator 11 to irradiate the eyeground 100B with a short-pulse laser beam, to excite the AOI which is a fluorescent dye bonded to amyloid β protein serving as a target at the eyeground 100B.

While taking the time point of emission of the laser beam as a reference, the fluorescence image acquisition apparatus 1 measures the fluorescence intensities I1 and I2 of the AOI at two different times t1 and t2 which are predetermined periods of time after the reference, through the photodetector 20.

In the fluorescence image acquisition apparatus 1, the ratio between the fluorescence intensities I1 and I2 at times t1 and t2 is calculated, and is compared with a threshold which is so set that only the AOI which has been changed in fluorescence life through linkage with amyloid β protein can be detected. Then, the fluorescence image acquisition apparatus 1 generates a fluorescence image based on the detection results.

In this manner, the fluorescence image acquisition apparatus 1 forms a fluorescence image on which is reflected only the fluorescent dye (AOI) bonded to the amyloid β protein contained in the drusen present at the yellow spot. Consequently, the presence or absence of the amyloid β protein can be found out at an early stage.

In addition, since the fluorescence image acquisition apparatus 1 uses the ratio between the fluorescence intensities I1 and I2 at times t1 and t2, the AOI bonded to the amyloid β protein can be detected, not depending on the fluorescence intensities at the time points of measurement but depending only on the life of fluorescence.

As compared with the observation of drusen by the fundus camera according to the related art, the fluorescence image acquisition apparatus 1, in which the fluorescence of the fluorescent dye (AOI) bonded to amyloid β protein is observed, makes it possible to find the drusen at a stage where the drusen is smaller and, therefore, to find the drusen at an earlier stage and with high accuracy.

Besides, since the fluorescence image acquisition apparatus 1 detects only the fluorescent dye (AOI) bonded to amyloid β protein by use of the ratio between the fluorescence intensities I1 and I2 at times t1 and t2, the fluorescent dye (AOI) floating without being bonded to amyloid β protein can be excluded from the fluorescence image.

Thus, according to the fluorescence image acquisition apparatus 1, the fluorescent dye (AOI) floating without being bonded to amyloid β protein is not reflected on the fluorescence image. This ensures that the presence or absence of amyloid β protein can be found more accurately.

Moreover, according to the fluorescence image acquisition apparatus 1, even if the acquisition of the fluorescence image is not after a predetermined lapse of time (120 minutes) from the dosing of the subject with the fluorescent dye (AOI), the fluorescent dye (AOI) not bonded to amyloid β protein is prevented from being reflected on the fluorescence image. Therefore, it is possible to shorten the waiting time until the start of imaging, that is, the examination time.

Meanwhile, the fluorescent marker compounds bonded specifically to amyloid β protein are mostly excited by ultraviolet rays. However, where the eyeground is irradiated with ultraviolet rays, the ultraviolet rays cannot easily reach the eyeground because they are absorbed by the cornea and the crystalline lens. In the case of acquiring a fluorescence image by use of ultraviolet rays, therefore, the intensity of the ultraviolet rays should be high, which imposes burden on the subject's eye.

On the other hand, the fluorescence image acquisition apparatus 1 uses a laser beam with a wavelength in the infrared region, for example, at 633 [nm]. Thus, notwithstanding the weak energy of the beam, the beam reaches the eyeground 100B securely and the fluorescence image can be acquired. Accordingly, the burden on the subject's eye can be alleviated greatly.

According to the above-described configuration, the eyeground 100B is irradiated with a short-pulse laser beam for exciting the fluorescent dye which is changed in fluorescence life through linkage to amyloid β protein present as a target. Then, while taking the time point of emission of the laser beam as a reference, the fluorescence intensities I1 and I2 at two different times t1 and t2 which are predetermined periods of time after the reference are measured, and a fluorescence image of the fluorescent dye bonded to the target is generated based on the ratio between the fluorescence intensities I1 and I2 at times t1 and t2.

As a result, the fluorescence image acquisition apparatus 1 generates a fluorescence image on which is reflected only the fluorescent dye (AOI) bonded to the amyloid β protein contained in the drusen present at the yellow spot. Accordingly, the presence/absence of the drusen can be found out at an early stage and accurately.

2. Another Embodiment

In the above-described embodiment, the ratio between the fluorescence intensities at times t1 and t2 is calculated, and, when the ratio is not less than a threshold, the fluorescent dye in question is detected as the fluorescent dye bonded to amyloid β protein. Then, based on the detection results, a fluorescence image is generated, as above-described. However, a fluorescence image may be generated based on the fluorescence intensity after a predetermined lapse of time from the emission of the laser beam.

Specifically, upon receiving a command for acquisition of a fluorescence image from the console unit 34, the CPU 31 deploys a program corresponding to the acquisition command into the RAM 33, and executes a process according to a flow chart shown in FIG. 6. Incidentally, in this case, a femtosecond laser may be applied as the short-pulse laser 12.

In practice, the CPU 31 starts control from a START step of routine RT2, and goes to the next step SP11. In step SP11, the CPU 31 inputs information that PIB is administered into the subject, for example, through the console unit 34, and goes to the subsequent step SP12. Incidentally, in the case where PIB is used in place of AOI, specifically, a femtosecond laser is used for excitation, an excitation wavelength of 800 [nm] is used, and a wavelength of fluorescence to be acquired is 400 to 450 [nm].

In step SP12, the CPU 31 notifies the user, for example through the display unit 36, that measurement can be started when a predetermined period of time (120 minutes) necessary for PIB to be excreted has passed from the input operation in step SP11. Then, the CPU 31 goes to the next step SP13.

In step SP13, the CPU 31 drives the XY scanner 17A to move so that a predetermined position is irradiated with a laser beam, then goes to the subsequent step SP14.

In step SP14, the CPU 31 sends an output signal to the signal generator 11, whereby the short-pulse laser 12 is actuated through the signal generator 11 to emit a short-pulse laser beam. Thereafter, the CPU 31 goes to the next step SP15.

In step SP15, the CPU 31 acquires a fluorescence intensity measured by the photodetector 20 after a predetermined lapse of time from the time point of supply of the emission signal from the signal generator 11, and then goes to the subsequent step SP16.

In step SP16, the CPU 13 determines whether or not the fluorescence intensities at all positions within an imaging range have been acquired. When the determination result is negative (NO), the control returns to step SP13, and steps SP13 to SP16 are repeated until the fluorescence intensities at all positions are acquired.

On the other hand, when the determination result of step SP16 is affirmative (YES), it means that the fluorescence intensities at all positions in the imaging range have been obtained, and the CPU 31 goes to the next step SP17.

In step SP17, the CPU 31 generates a fluorescence image based on the relationship between the positions of scan of the laser beam by the XY scanner 17A and the fluorescence intensities measured by the photodetector 20, and goes to the subsequent step, finishing the process.

Thus, the fluorescence image acquisition apparatus 1 generates a fluorescence image of only the PIB bonded to amyloid β protein, even through the fluorescence image is generated based on the fluorescence intensities after a predetermined lapse of time from the emission of the laser beam. Consequently, the amyloid β protein can be found at an early stage and with high accuracy.

In the embodiments as above-described, the fluorescent dye capable of being bonded to amyloid β protein has been used, and the presence/absence of amyloid β protein has been thereby detected. However, this is not limitative; for example, other protein present at the eyeground may be used as a target, while using a fluorescent dye which is capable of being bonded specifically to the target protein and which is changed in fluorescence life through the specific linkage.

In the above embodiments, use has been made of the fluorescent dye which is changed in fluorescence life through bonding to amyloid β protein. However, this is not limitative. For example, a fluorescent dye which is changed in wavelength of fluorescence through linkage with amyloid β protein may be used, and a fluorescence image may be formed by imaging the fluorescence of the wavelength generated upon the linkage.

Further, in the above-described embodiments, the CPU 31 has executed the above-mentioned fluorescence image acquisition process according to a program stored in the ROM 32. However, the fluorescence image acquisition process may be carried out according to a program which is installed from a recording medium or downloaded from the Internet. Besides, the above-mentioned fluorescence image acquisition process may be performed according to programs installed through a variety of other routes.

Furthermore, in the above embodiments, a configuration has been adopted in which the short-pulse laser 12 is provided as the light source, the drive control section 41 is provided as the light source control section, the detection section 44 is provided as the detection section, and the image acquisition section 45 is provided as the generation section. However, a light source, a light source control section, a detection section and a generation section with other various configurations may be provided.

The present embodiments are applicable to bio-industries such as bio-experiments, observation of developments after treatment of a patient, etc.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A fluorescence image acquisition method comprising:
   irradiating an eyeground that has been provided with a fluorescent dye with a short-pulse beam of light for exciting the fluorescent dye;
   setting the time point of emission of the light as a reference, measuring the intensities of luminescence of the fluorescent dye at two different times which are predetermined periods of time after the reference;
   determining the ratio between the intensities of luminescence at the two different times;
   comparing the determined ratio with a threshold value to determine if the fluorescent dye has bonded to a target and, based thereon, detecting the position of the target; and
   generating a fluorescence image of the fluorescent dye after having marked the target, based on the results of the detection by the detecting step.

2. The fluorescence image acquisition method according to claim 1, wherein the fluorescence dye is varied in life of fluorescence when the target is marked therewith.

3. The fluorescence image acquisition method according to claim 1, wherein the eyeground is irradiated with a short-pulse beam of light in an infrared region.

4. A fluorescence image acquisition non-transitory computer program product including executable instructions that when executed by a processor perform steps for:
   irradiating an eyeground that has been provided with a fluorescent dye with a short-pulse beam of light for exciting the fluorescent dye;
   setting the time point of emission of the light as a reference, measuring the intensities of luminescence of the fluorescent dye at two different times which are predetermined periods of time after the reference;
   determining the ratio between the intensities of luminescence at the two different times;
   comparing the determined ratio with a threshold value to determine if the fluorescent dye has bonded to a target and, based thereon, detecting the position of the target; and
   generating a fluorescence image of the fluorescent dye after having marked the target, based on the results of the detection by the detecting step.

5. A fluorescence image acquisition apparatus comprising:
   a light source operable to emit a short-pulse beam of light for exciting a fluorescent dye that has been provided to an eyeground;
   a light source control section operable to irradiate the eyeground with the light from the light source;
   a detection section operable to
     set the time point of emission of the light as a reference,
     measure the intensities of luminescence of the fluorescent dye at two different times which are predetermined periods of time after the reference,
     determine the ratio between the intensities of luminescence at the two different times, and
     compare the determined ratio with a threshold value to determine if the fluorescent dye has bonded to a target and, based thereon, detect the position of the target; and
   a generation section operable to generate a fluorescence image of the fluorescent dye after having marked the target, based on the results of the detection by the detection section.

* * * * *